US012792130B2

(12) United States Patent
Vemparala Guruswamy et al.

(10) Patent No.: US 12,792,130 B2
(45) Date of Patent: Nov. 10, 2026

(54) SMART NOSE WITH MACHINE LEARNING

(71) Applicant: Micron Technology, Inc., Boise, ID (US)

(72) Inventors: Priya Vemparala Guruswamy, Boise, ID (US); Barbara J. Bailey, Kuna, ID (US); Marsela Pontoh, Boise, ID (US); Aparna U. Limaye, Boise, ID (US); Tejas Jagadeesh, Bothell, WA (US)

(73) Assignee: Micron Technology, Inc., Boise, ID (US)

( * ) Notice: Subject to any disclaimer, the term of this patent is extended or adjusted under 35 U.S.C. 154(b) by 316 days.

(21) Appl. No.: 18/438,912

(22) Filed: Feb. 12, 2024

(65) Prior Publication Data

US 2024/0272703 A1 Aug. 15, 2024

Related U.S. Application Data

(60) Provisional application No. 63/445,424, filed on Feb. 14, 2023.

(51) Int. Cl.
*G06F 3/01* (2006.01)
*G01N 33/00* (2006.01)
*G06V 10/10* (2022.01)

(52) U.S. Cl.
CPC ......... *G06F 3/011* (2013.01); *G01N 33/0034* (2013.01); *G06V 10/10* (2022.01)

(58) Field of Classification Search
CPC ...... G06F 3/011; G06V 10/10; G01N 33/0034
See application file for complete search history.

(56) References Cited

U.S. PATENT DOCUMENTS

| | | | | |
|---|---|---|---|---|
| 7,640,116 | B2 | 12/2009 | Duong | |
| 10,592,510 | B2 * | 3/2020 | Nose | G06F 16/2455 |
| 10,928,369 | B2 | 2/2021 | Herrier | |
| 2006/0191319 | A1 | 8/2006 | Kurup | |
| 2013/0061692 | A1 | 3/2013 | Muresan | |
| 2022/0091083 | A1 | 3/2022 | Ivanov | |

FOREIGN PATENT DOCUMENTS

| | | | |
|---|---|---|---|
| JP | 2019168887 A | * 10/2019 | G06Q 10/04 |

* cited by examiner

*Primary Examiner* — Matthew James Bodnark
(74) *Attorney, Agent, or Firm* — Brooks, Cameron & Huebsch, PLLC

(57) ABSTRACT

Methods, apparatuses, and systems associated with a smart nose with machine learning are described. A system can include a smart nose device configured to receive an odor and create a first odor vector associated with the odor. The system can include an image detection device configured to receive a plurality of images while the odor is received and identify a plurality of objects within the plurality of images. The system can also include a computing device to refine the first odor vector based on the identified plurality of objects, create, utilizing a machine learning model, a second odor vector based on the refined first odor vector and an odor pattern database, and predict the odor based on the second odor vector.

18 Claims, 6 Drawing Sheets

560 INPUT FEATURES

562 PREDICTION RESPONSE

| COMBO VECTORS | ODORANT 1 | ODORANT 2 | ..... | ODORANT 399 | ODORANT 400 | OBJECT LIST |
|---|---|---|---|---|---|---|
| CAKE FV | 1 | 0 | ..... | 1 | 1 | CAKE |
| CAKE PV1 | 0 | 1 | ..... | 1 | 0 | CAKE |
| CAKE PV2 | 0 | 1 | ..... | 0 | 1 | CAKE |
| ROSE FV | 0 | 1 | ..... | 0 | 1 | ROSE |
| ROSE PV1 | 0 | 1 | ..... | 0 | 0 | ROSE |
| CAKE FV + ROSE FV | 1 | 1 | ..... | 1 | 1 | CAKE, ROSE |
| CAKE FV + ROSE PV1 | 1 | 1 | | 1 | 1 | CAKE, ROSE |
| CAKE PV1 + ROSE FV | 0 | 1 | | 1 | 1 | CAKE, ROSE |
| CAKE PV1 + ROSE PV1 | 0 | 1 | | 1 | 0 | CAKE, ROSE |

FV: FULL ODOR VECTOR
PV1, PV2: DIFFERENT PARTIAL ODOR VECTORS
FV+FV, FV+PV, PV+PV: COMBINATION ODOR VECTORS

FIG. 5

SMART NOSE WITH MACHINE LEARNING

PRIORITY INFORMATION

This Application claims the benefits of U.S. Provisional Application No. 63/445,424, filed on Feb. 14, 2023, the contents of which are incorporated herein by reference.

TECHNICAL FIELD

The present disclosure relates generally to apparatuses, systems, and methods associated with a smart nose and image recognition, including the use of machine learning.

BACKGROUND

Memory resources are typically provided as internal, semiconductor, integrated circuits in computers or other electronic systems. There are many different types of memory, including volatile and non-volatile memory. Volatile memory can require power to maintain its data (e.g., host data, error data, etc.). Volatile memory can include random access memory (RAM), dynamic random-access memory (DRAM), static random-access memory (SRAM), synchronous dynamic random-access memory (SDRAM), and thyristor random access memory (TRAM), among other types. Non-volatile memory can provide persistent data by retaining stored data when not powered. Non-volatile memory can include NAND flash memory, NOR flash memory, and resistance variable memory, such as phase change random access memory (PCRAM) and resistive random-access memory (RRAM), ferroelectric random-access memory (FeRAM), and magnetoresistive random access memory (MRAM), such as spin torque transfer random access memory (STT RAM), among other types.

Electronic systems often include a number of processing resources (e.g., one or more processing resources), which may retrieve instructions from a suitable location and execute the instructions and/or store results of the executed instructions to a suitable location (e.g., the memory resources). A processing resource can include a number of functional units such as arithmetic logic unit (ALU) circuitry, floating point unit (FPU) circuitry, and a combinatorial logic block, for example, which can be used to execute instructions by performing logical operations such as AND, OR, NOT, NAND, NOR, and XOR, and invert (e.g., NOT) logical operations on data (e.g., one or more operands). For example, functional unit circuitry may be used to perform arithmetic operations such as addition, subtraction, multiplication, and division on operands via a number of operations.

Machine learning can be used in conjunction with memory resources. As described herein, the term "machine learning" refers to a process by which a computing device is able to improve its own performance through iterations by continuously incorporating new data into an existing statistical model. Machine learning can facilitate automatic learning for computing devices without human intervention or assistance and adjust actions accordingly.

BRIEF DESCRIPTION OF THE DRAWINGS

FIG. 5 is diagram including example machine learning model training inputs in accordance with a number of embodiments of the present disclosure.

DETAILED DESCRIPTION

Figure 1:
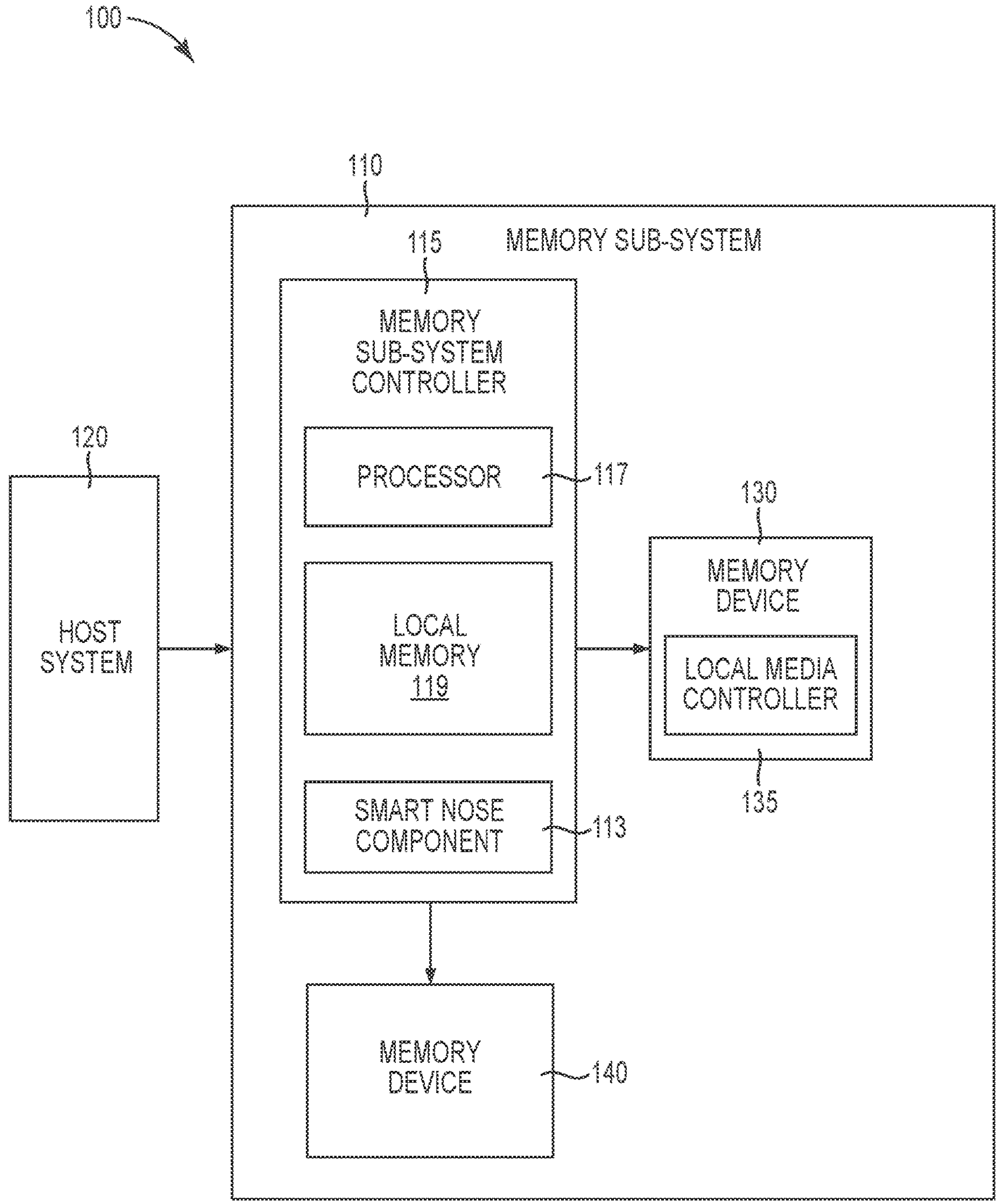
FIG. 1 illustrates an example computing system that includes a memory sub-system in accordance with a number of embodiments of the present disclosure.

Systems, devices, and methods related to a smart nose with machine learning are described. Humans have hundreds of odor receptors that help them detect odors. There are odors that are not detectable by the human nose, however. Additionally, some humans are unable to smell some or all odors due to different conditions such as anosmia, among others. Further, some odors may be dangerous, but these odors may not be detectable by the human nose, in some instances. In such instances, a smart nose may be utilized.

A smart nose, also known as an electronic nose (e.g., "e-nose") or an artificial nose, among others, is a device trained to recognize smells. For instance, a smart nose can include an array of sensors that help in mimicking the olfactory system and can be used to aid humans with reduced, limited, or no smelling ability and/or may be used in workplaces for various purposes. A smart nose may work for patterns previously identified and signals previously decoded. A previously unidentified odor may not be detected, in such examples. These examples may include a limited number of recognizable odors and/or may lack updating, for instance via a feedback loop.

Examples of the present disclosure can allow for the odor detection utilizing a smart nose device with machine learning. For instance, a machine learning model can utilize results from the smart nose combined with image recognition results to enable context-based identification and mapping of odors, as well as updating of odor pattern databases. This can enhance a prediction and determine an activation pattern the brain should see for the particular odor and/or an activation pattern indicating an unsafe odor, unsafe object, and/or odor to block. For instance, two objects may have similar odors that a smart nose cannot differentiate. However, if a user can see the object, for instance while wearing smart glasses, the image recognition of the object plus the odor detected at the smart nose can improve accuracy of the activation pattern determination and resulting odor prediction.

A feedback loop can be utilized to update the machine learning model and/or the odor pattern databases to improve accuracy of odor predictions, determinations, etc. Examples can allow for choices regarding allowed and blocked odors, as well as for alerts for dangerous objects and/or associated odors (e.g., dangerous animals, chemicals, gases, etc.). A cloud-based database can be utilized to update machine learning models and databases (e.g., odor pattern databases including odor vectors, odor safety databases, etc.) based on real time user experience, and an electrical signature can be created for recognized images and odor signals (e.g., odor vectors). Users may provide input indicating correct, incorrect, and/or incomplete odor identification, in some instances.

Activation pattern information, image recognition information, odor vector information, etc. can be stored in cloud storage making the different information available and accessible. The device may include local memory storage, in some examples, so the smart nose and image recognition can be utilized when no internet connection is available. The local storage can be updated when in communication with the cloud storage, for example.

Examples of the present disclosure can include a system comprising a smart nose device configured to receive an odor and create a first odor vector associated with the odor. The system can include an image detection device configured to receive a plurality of images while the odor is received and identify a plurality of objects within the plurality of images. The system can also include a computing device to refine the first odor vector based on the identified plurality of objects, create, utilizing a machine learning model, a second odor vector based on the refined first odor vector and an odor pattern database, predict the odor based on the second odor vector. Examples can include sending the prediction to a brain implant or providing an alert based on the predicted odor, among others.

In the following detailed description of the present disclosure, reference is made to the accompanying drawings that form a part hereof, and in which is shown by way of illustration how one or more embodiments of the disclosure can be practiced. These embodiments are described in sufficient detail to enable those of ordinary skill in the art to practice the embodiments of this disclosure, and it is to be understood that other embodiments can be utilized and that process, electrical, and structural changes can be made without departing from the scope of the present disclosure.

It is also to be understood that the terminology used herein is for the purpose of describing particular embodiments only and is not intended to be limiting. As used herein, the singular forms "a," "an," and "the" can include both singular and plural referents, unless the context clearly dictates otherwise. In addition, "a number of," "at least one," and "one or more" (e.g., a number of memory devices) can refer to one or more memory devices, whereas a "plurality of" is intended to refer to more than one of such things. Furthermore, the words "can" and "may" are used throughout this application in a permissive sense (i.e., having the potential to, being able to), not in a mandatory sense (i.e., must). The term "include," and derivations thereof, means "including, but not limited to." The terms "coupled," and "coupling" mean to be directly or indirectly connected physically or for access to and movement (transmission) of commands and/or data, as appropriate to the context.

The figures herein follow a numbering convention in which the first digit or digits correspond to the figure number and the remaining digits identify an element or component in the figure. Similar elements or components between different figures can be identified by the use of similar digits. For example, 218 can reference element "18" in FIG. 2, and a similar element can be referenced as 318 in FIG. 3. As will be appreciated, elements shown in the various embodiments herein can be added, exchanged, and/or eliminated so as to provide a number of additional embodiments of the present disclosure. In addition, the proportion and/or the relative scale of the elements provided in the figures are intended to illustrate certain embodiments of the present disclosure and should not be taken in a limiting sense.

FIG. 1 illustrates an example computing system 100 that includes a memory sub-system 110 in accordance with a number of embodiments of the present disclosure. The memory sub-system 110 can include media, such as one or more volatile memory devices (e.g., memory device 140), one or more non-volatile memory devices (e.g., memory device 130), or a combination of such.

A memory sub-system 110 can be a storage device, a memory module, or a hybrid of a storage device and memory module. Examples of a storage device include a solid-state drive (SSD), a flash drive, a universal serial bus (USB) flash drive, an embedded Multi-Media Controller (eMMC) drive, a Universal Flash Storage (UFS) drive, a secure digital (SD) card, and a hard disk drive (HDD). Examples of memory modules include a dual in-line memory module (DIMM), a small outline DIMM (SO-DIMM), and various types of non-volatile dual in-line memory modules (NVDIMMs).

The computing system 100 can be a computing device such as a desktop computer, laptop computer, server, network server, mobile device, a vehicle (e.g., airplane, drone, train, automobile, or other conveyance), Internet of Things (IoT) enabled device, embedded computer (e.g., one included in a vehicle, industrial equipment, or a networked commercial device), or such computing device that includes memory and a processing device.

The computing system 100 can include a host system 120 that is coupled to one or more memory sub-systems 110. In some embodiments, the host system 120 is coupled to different types of memory sub-system 110. FIG. 1 illustrates one example of a host system 120 coupled to one memory sub-system 110. As used herein, "coupled to" or "coupled with" generally refers to a connection between components, which can be an indirect communicative connection or direct communicative connection (e.g., without intervening components), whether wired or wireless, including connections such as electrical, optical, magnetic, and the like.

The host system 120 can include a processor chipset and a software stack executed by the processor chipset. The processor chipset can include one or more cores, one or more caches, a memory controller (e.g., an SSD controller), and a storage protocol controller (e.g., PCIe controller, SATA controller). The host system 120 uses the memory sub-system 110, for example, to write data to the memory sub-system 110 and read data from the memory sub-system 110.

The host system 120 can be coupled to the memory sub-system 110 via a physical host interface. Examples of a physical host interface include, but are not limited to, a serial advanced technology attachment (SATA) interface, a peripheral component interconnect express (PCIe) interface, universal serial bus (USB) interface, Fibre Channel, Serial Attached SCSI (SAS), Small Computer System Interface (SCSI), a double data rate (DDR) memory bus, a dual in-line memory module (DIMM) interface (e.g., DIMM socket interface that supports Double Data Rate (DDR)), Open NAND Flash Interface (ONFI), Double Data Rate (DDR), Low Power Double Data Rate (LPDDR), or any other interface. The physical host interface can be used to transmit data between the host system 120 and the memory sub-system 110. The host system 120 can further utilize an NVM Express (NVMe) interface to access components (e.g., memory devices 130) when the memory sub-system 110 is coupled with the host system 120 by the PCIe interface. The physical host interface can provide an interface for passing control, address, data, and other signals between the memory sub-system 110 and the host system 120. FIG. 1 illustrates a memory sub-system 110 as an example. In general, the host system 120 can access multiple memory sub-systems via the same communication connection, multiple separate communication connections, and/or a combination of communication connections.

The memory devices 130, 140 can include any combination of the different types of non-volatile memory devices and/or volatile memory devices. The volatile memory devices (e.g., memory device 140) can be, but are not limited to, random access memory (RAM), such as dynamic random-access memory (DRAM) and synchronous dynamic random-access memory (SDRAM).

Some examples of non-volatile memory devices (e.g., memory device 130) include negative-and (NAND) type flash memory and write-in-place memory, such as three-dimensional cross-point ("3D cross-point") memory device, which is a cross-point array of non-volatile memory cells. A cross-point array of non-volatile memory can perform bit storage based on a change of bulk resistance, in conjunction with a stackable cross-gridded data access array. Additionally, in contrast to many flash-based memories, cross-point non-volatile memory can perform a write in-place operation, where a non-volatile memory cell can be programmed without the non-volatile memory cell being previously erased. NAND type flash memory includes, for example, two-dimensional NAND (2D NAND) and three-dimensional NAND (3D NAND).

Each of the memory devices 130, 140 can include one or more arrays of memory cells. One type of memory cell, for example, single level cells (SLC) can store one bit per cell. Other types of memory cells, such as multi-level cells (MLCs), triple level cells (TLCs), quad-level cells (QLCs), and penta-level cells (PLC) can store multiple bits per cell. In some embodiments, each of the memory devices 130 can include one or more arrays of memory cells such as SLCs, MLCs, TLCs, QLCs, or any combination of such. In some embodiments, a particular memory device can include an SLC portion, and an MLC portion, a TLC portion, a QLC portion, or a PLC portion of memory cells. The memory cells of the memory devices 130 can be grouped as pages that can refer to a logical unit of the memory device used to store data. With some types of memory (e.g., NAND), pages can be grouped to form blocks.

Although non-volatile memory components such as three-dimensional cross-point arrays of non-volatile memory cells and NAND type memory (e.g., 2D NAND, 3D NAND) are described, the memory device 130 can be based on any other type of non-volatile memory or storage device, such as, read-only memory (ROM), phase change memory (PCM), self-selecting memory, other chalcogenide based memories, ferroelectric transistor random-access memory (FeTRAM), ferroelectric random access memory (FeRAM), magneto random access memory (MRAM), Spin Transfer Torque (STT)-MRAM, conductive bridging RAM (CBRAM), resistive random-access memory (RRAM), oxide based RRAM (OxRAM), negative-or (NOR) flash memory, and electrically erasable programmable read-only memory (EEPROM).

The memory sub-system controller 115 (or controller 115 for simplicity) can communicate with the memory devices 130 to perform operations such as reading data, writing data, or erasing data at the memory devices 130 and other such operations. The memory sub-system controller 115 can include hardware such as one or more integrated circuits and/or discrete components, a buffer memory, or a combination thereof. The hardware can include digital circuitry with dedicated (i.e., hard-coded) logic to perform the operations described herein. The memory sub-system controller 115 can be a microcontroller, special purpose logic circuitry (e.g., a field programmable gate array (FPGA), an application specific integrated circuit (ASIC), etc.), or another suitable processor.

The memory sub-system controller 115 can include a processor 117 (e.g., a processing device) configured to execute instructions stored in a local memory 119. In the illustrated example, the local memory 119 of the memory sub-system controller 115 includes an embedded memory configured to store instructions for performing various processes, operations, logic flows, and routines that control operation of the memory sub-system 110, including handling communications between the memory sub-system 110 and the host system 120.

In some embodiments, the local memory 119 can include memory registers storing memory pointers, fetched data, etc. The local memory 119 can also include read-only memory (ROM) for storing micro-code. While the example memory sub-system 110 in FIG. 1 has been illustrated as including the memory sub-system controller 115, in another embodiment of the present disclosure, a memory sub-system 110 does not include a memory sub-system controller 115, and can instead rely upon external control (e.g., provided by an external host, or by a processor or a controller separate from the memory sub-system).

In general, the memory sub-system controller 115 can receive commands or operations from the host system 120 and can convert the commands or operations into instructions or appropriate commands to achieve the desired access to the memory device 130 and/or the memory device 140. The memory sub-system controller 115 can be responsible for other operations such as wear leveling operations, garbage collection operations, error detection and error-correcting code (ECC) operations, encryption operations, caching operations, and address translations between a logical address (e.g., logical block address (LBA), namespace) and a physical address (e.g., physical block address, physical media locations, etc.) that are associated with the memory devices 130. The memory sub-system controller 115 can further include host interface circuitry to communicate with the host system 120 via the physical host interface. The host interface circuitry can convert the commands received from the host system into command instructions to access the memory device 130 and/or the memory device 140 as well as convert responses associated with the memory device 130 and/or the memory device 140 into information for the host system 120.

The memory sub-system 110 can also include additional circuitry or components that are not illustrated. In some embodiments, the memory sub-system 110 can include a cache or buffer (e.g., DRAM) and address circuitry (e.g., a row decoder and a column decoder) that can receive an address from the memory sub-system controller 115 and decode the address to access the memory device 130 and/or the memory device 140.

In some embodiments, the memory device 130 includes local media controllers 135 that operate in conjunction with memory sub-system controller 115 to execute operations on one or more memory cells of the memory devices 130. An external controller (e.g., memory sub-system controller 115) can externally manage the memory device 130 (e.g., perform media management operations on the memory device 130). In some embodiments, a memory device 130 is a managed memory device, which is a raw memory device combined with a local controller (e.g., local controller 135) for media management within the same memory device package. An example of a managed memory device is a managed NAND (MNAND) device.

The memory sub-system 110 can include a smart nose component 113. Although not shown in FIG. 1 so as to not obfuscate the drawings, the smart nose component 113 can include various circuitry to facilitate odor detection. In some embodiments, the smart nose component 113 can include special purpose circuitry in the form of an ASIC, FPGA, state machine, and/or other logic circuitry that can allow the smart nose component 113 to orchestrate and/or perform odor detection and image recognition operations, as discussed further herein.

In some embodiments, the memory sub-system controller 115 includes at least a portion of the smart nose component 113. For example, the memory sub-system controller 115 can include a processor 117 (processing device) configured to execute instructions stored in local memory 119 for performing the operations described herein. In some embodiments, the smart nose component 113 is part of the host system 110, an application, or an operating system.

In a non-limiting example, an apparatus (e.g., the computing system 100) can include a memory sub-system smart nose component 113. The memory sub-system smart nose component 113 can be resident on the memory sub-system 110. As used herein, the term "resident on" refers to something that is physically located on a particular component. For example, the memory sub-system smart nose component 113 being "resident on" the memory sub-system 110 refers to a condition in which the hardware circuitry that comprises the memory sub-system smart nose component 113 is physically located on the memory sub-system 110. The term "resident on" can be used interchangeably with other terms such as "deployed on" or "located on," herein.

The smart nose component 113 can use a machine learning model or models to determine a particular odor and associated object. For instance, the smart nose component 113 can determine which odors match which objects when partial or full odor vectors are present. The odor and object can be presented to a user or an alert of an unsafe odor can be provided to the user.

The smart nose component 113 can include, for instance, a machine learning model such as a tabular data machine learning model (e.g., tree-based machine learning model) that performs multi-class classification on tabular data (e.g. numerical data, categorical data, etc.), an image data machine learning model (e.g., a convolution neural network machine learning model) to perform multi-class classification on image data (e.g., videos, images, video clips, image sequences, etc.), or both. Other machine learning models and/or combinations thereof may be part of the smart nose component 113. The smart nose component 113 can include, in some examples, a processing resource in communication with a memory resource that utilizes the machine learning model(s) to detect an odor. Put another way, the smart nose component 113 and associated machine learning models determine an odor associated with a particular object and/or determines the odor is unsafe based on data available to the smart nose component 113 including, but not limited to, image data, manual data, and user feedback.

The smart nose component 113 and associated machine learning model(s) can be trained using a training dataset or training datasets. For instance, a training dataset can include a set of examples used to fit parameters of the machine learning models. For instance, the training dataset for the machine learning model(s) can include data associated with image data from a plurality of sources including, for example, an image database including object images, an object feature image database including object features and/or images of object features, still images of locations, video data of locations, image sequence data from video data, or a combination thereof. The image database may be local to a device or may be cloud-based, in some examples.

The training dataset can also include data associated with manual data, such as object data (e.g., unique features, colors, etc.) or location data manually entered into the tool or a database associated therewith, and user requests for odor detection and feedback associated therewith. In some examples, the smart nose component 113 and associated machine learning model(s) can also be trained using new input data (e.g., new data from databases, users, research data, etc., among others). In some examples, the smart nose component 113 and associated trained machine learning model(s) can include continuous learning of the machine learning model(s) and re-calibration of the machine learning model(s).

Figure 2:
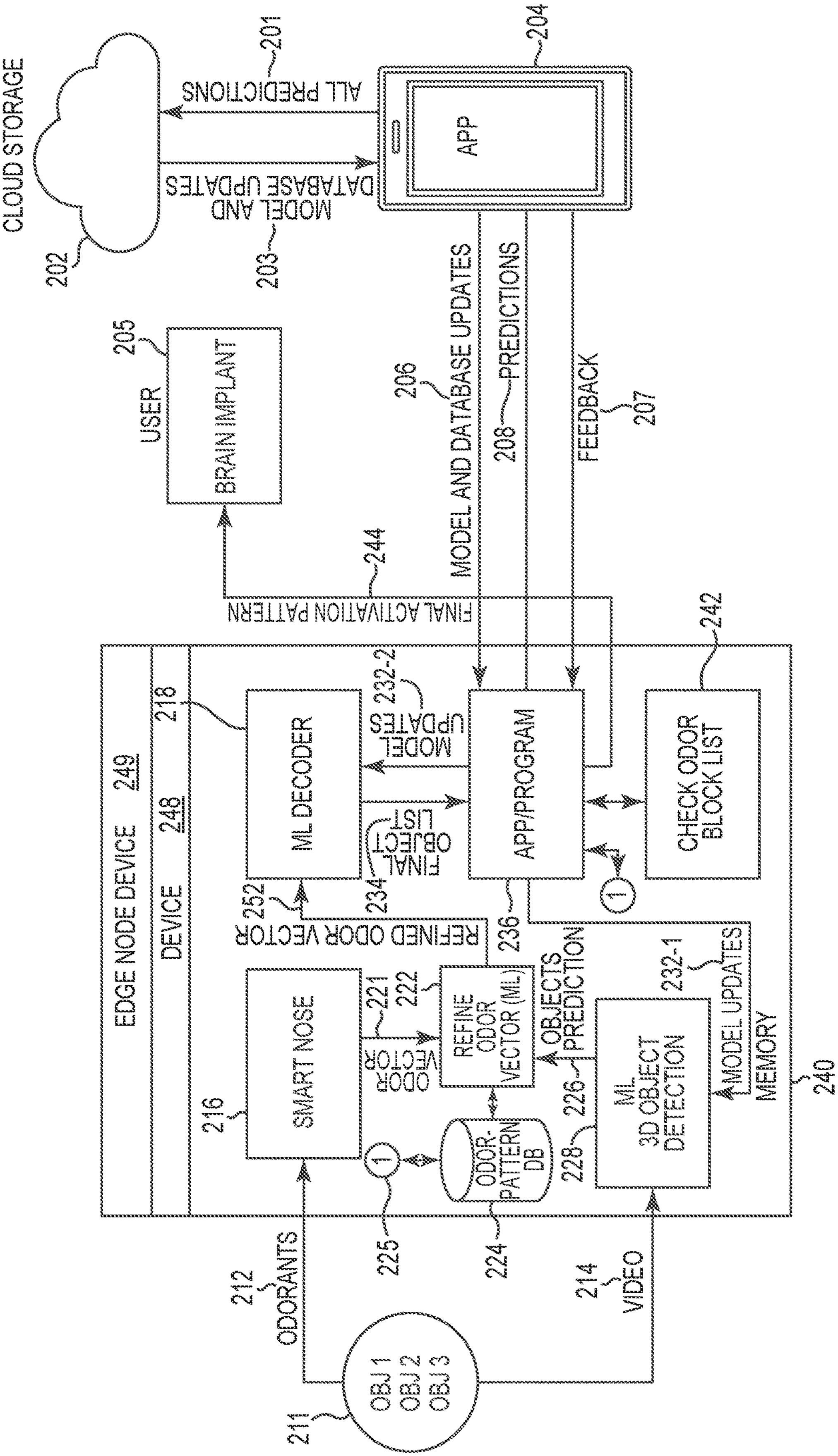
FIG. 2 is functional diagram representing a device including a smart nose with machine learning in accordance with a number of embodiments of the present disclosure.

FIG. 2 is functional diagram representing a device 248 including a smart nose 216 with machine learning in accordance with a number of embodiments of the present disclosure. In the example illustrated in FIG. 2, a user may carry or wear the device 248 that includes the smart nose 216 and an image recognition device 228 (e.g., camera, smart glasses, smart lenses, smart phone, etc.). In some examples, the image recognition device 228 can be in communication with security cameras to collect images and/or video. The device 248 may include a processor, such as the processor 117 described with respect to FIG. 1 and may include an edge node device 249 for interaction with external devices such as cloud storage 202 and the mobile device having an application 204 thereon.

The processor may be in communication with a memory device, such as the memory devices described with respect to FIG. 1. The memory device (e.g., a non-transitory machine-readable medium (MRM)), may have stored thereon instructions. The device 248, in some examples, may be analogous to smart nose component 113 and/or the device 350 described with respect to FIG. 3. Although the following descriptions refer to a processor and a memory device, the descriptions may also apply to a system with multiple processing resources and multiple memory resources. In such examples, the instructions may be distributed (e.g., stored) across multiple memory resources and the instructions may be distributed (e.g., executed by) across multiple processing resources.

The memory device may be electronic, magnetic, optical, or other physical storage device that stores executable instructions. Thus, the memory device may be, for example, non-volatile or volatile memory. In some examples, the memory device is a non-transitory MRM comprising RAM, an Electrically-Erasable Programmable ROM (EEPROM), a storage drive, an optical disc, and the like. The memory device may be disposed within a controller and/or computing device. In this example, the executable instructions can be "installed" on the device 248. Additionally, and/or alternatively, the memory device can be a portable, external or remote storage medium, for example, that allows the system to download the instructions from the portable/external/remote storage medium. In this situation, the executable instructions may be part of an "installation package". As described herein, the memory device can be encoded with executable instructions for odor detection.

The smart nose 216 (e.g., a smart nose device, electronic nose, e-nose, artificial nose, etc.) can include a plurality of sensors for different odor receptors and can capture odorants 212 given off and/or produced by objects 1, 2, and 3 211. The smart nose 216 can create a combined odor vector 221 based on the odorants 212. For instance, the smart nose device 216 can receive an odor (e.g., also referred to as an "odorant") and create a first odor vector associated with the odor.

An image recognition device 228 (also referred to herein as an "image detection device") can scan an area including objects 1, 2, and 3 211 and collect video 214 and/or images of the objects 1, 2, and 3 211. The image recognition device 228 (e.g., a three-dimensional object detection device) can receive the video 214 or images and can run image recognition machine learning models based on the video 214 and/or images to identify and make a list of predicted objects 226 present (e.g., list including objects 1, 2, and 3 211). For example, the image detection device 228 can receive a plurality of images while the odor 212 is received, and the image detection device 228 can identify a plurality of objects (e.g., predicted objects 226) within the plurality of images using a machine learning algorithm, for instance. The image data can be received, in some instances, in real time. In some examples, the image data can be received as previously recorded images, videos, and image sequences.

The combined odor vector 221 and the list of predicted objects 226 can be fed into a refine odor vector machine learning model 222 to map odorants 212 to objects 1, 2, 3 211 using an odor pattern database 224. The odor pattern database 224 can include a list of substances with their corresponding odor vectors. When only a partial odor vector is present, the refine odor vector machine learning model 222 can correlate odor vectors to objects identified by the image recognition device 228 (e.g., objects 1, 2, and 3 211) to generate the refined odor vector 252, which includes a full odor vector. The odor pattern database 224 may be local to device 248, and can be updated responsive to connection to a cloud-based odor pattern database, such as cloud storage 202. In some examples, the odor pattern database 224 may be cloud-based.

The refined odor vector 252 can be fed into a machine learning decoder 218 for generation of a final object identification list 234, which is queried against the odor pattern database 224 via and application or program 236 to determine an activation pattern. Put another way, the first odor vector can be refined based on the identified plurality of objects (e.g., predicted objects 226), and utilizing a machine learning model, a second odor vector based on the refined first odor vector and the odor pattern database can be created. Based on this second odor vector, the odor can be predicted. For instance, if an odor is detected by the smart nose, but the odor could be for a first flower type or a second flower type, device 248 can use the images detected for context-based identification and mapping of the odor. If the first flower type is recognized by the image recognition device 228, but the second flower type is not, a prediction of the first flower type being the source of the odor is warranted.

In some examples, the application and/or program 236 can further validate the final object list 234 and associated activation pattern against an odor block list, which may include dangerous odors, odors a user does not desire to detect, etc. The final activation pattern 244, determined subsequent to checking the odor block list 242, can include a pattern of electrical impulses that are input into a brain implant 205 of the user. The final activation pattern 244 can trigger various neurons in the brain for the user to recognize the odor.

The device 248 can include an odor pattern database 224. The odor pattern database 224 can be local to the device 248 and can be accessible with or without an Internet connection. The odor pattern database 224 can be in communication with the application and/or program 236 and vice versa, as illustrated at connection 1 225. For instance, the application and/or program 236 can communicate via wireless or wired communication with the odor pattern database 224 based on the feedback 207 received by the application and/or program 236, model and database updates 203, 206 received by the application and/or program 236, and other determinations made regarding the machine learning models, odor vectors, object predictions, etc. Put another way, the application and/or program 236 can sync up to the cloud storage 202 via the device application 204 or via a wireless or wired connection, and the odor pattern database, located local to the device 248 can be updated via the connection 1 225 between the application and/or program 236 and the odor pattern database 224. The connection 1 225 can be a wireless or wired connection. Using the updated information received at the odor pattern database 224, the refine odor vector machine learning model 222 can be updated.

The application and/or program 236 can receive updates and feedback regarding the odorants 212. For instance, the cloud storage 202 can be updated with new and/or more accurate odor vectors, which can affect predictions 208 made regarding the odors 212. The updates, both to databases and machine learning models can be sent, at 203, to a mobile application 204 utilized by the user, and then passed along, at 206, to the device 248. For instance, the application and/or program 236 can receive updates to machine learning models and send them to appropriate locations, for instance at 232-2 to update a machine learning model used to predict final odor vectors and at 232-1 to update a machine learning model used in image recognition. The odor pattern database 224 may be updated, for instance, responsive to a predicted odor being absent from the odor pattern database 224, for instance via connection 1 225.

Other feedback can be sent to the device 248 at 207. For instance, if a user sees a prediction and knows it's incorrect, the user can flag it in the application 204, and the feedback at 207 can be used to update the machine learning models at 232-1, 232-2. The application 204 can also take the predictions 208 and update the machine learning models, odor vectors, etc. stored in cloud storage 202 with the predictions at 201. For instance, the cloud storage 202 can be updated based on real time user experience and an electrical signature (e.g., a unique electrical signature) can be created for each image and smell detected and/or predicted. The odor pattern database 224 may be updated, for instance, responsive to the predicted odor being absent from the odor pattern database 224, for instance via connection 1 225.

Figure 3:
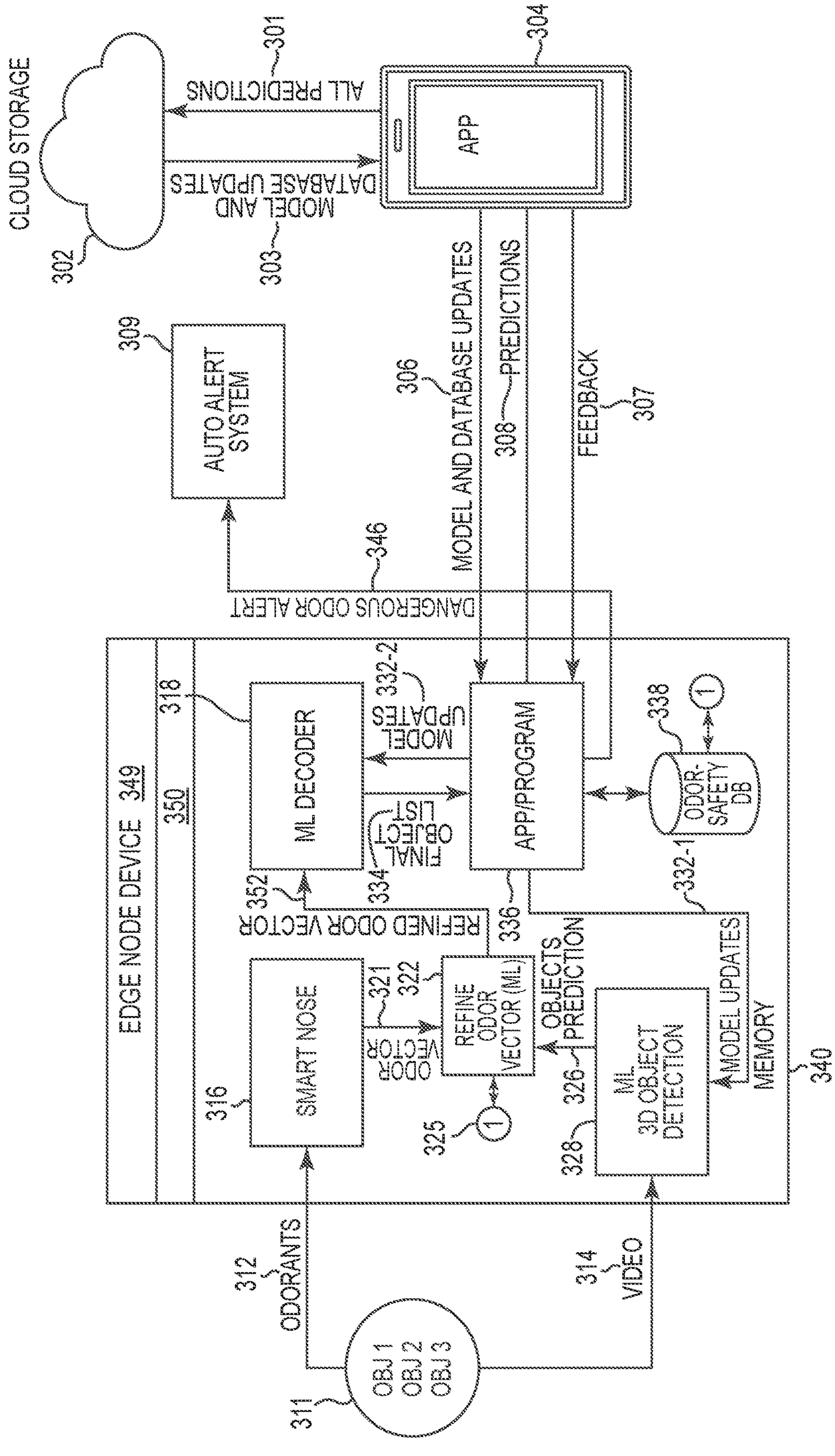
FIG. 3 is another functional diagram representing a device including a smart nose with machine learning in accordance with a number of embodiments of the present disclosure.

FIG. 3 is another functional diagram representing a device 350 including a smart nose 316 with machine learning in accordance with a number of embodiments of the present disclosure. In the example illustrated in FIG. 3, the device 350 that includes the smart nose device 316 and an image collection/detection device 328 (e.g., camera, smart glasses, smart lenses, smart phone, etc.). The device 350 may include a processor, such as the processor 117 described with respect to FIG. 1 and FIG. 2 and may include an edge node device 349 for interaction with external devices such as cloud storage 302 and the mobile device having an application 304 thereon.

The smart nose 316 (e.g., a smart nose device, electronic nose, e-nose, artificial nose, etc.) can include a plurality of sensors for different odor receptors and can capture odorants 312 given off and/or produced by objects 1, 2, and 3 311. The smart nose 316 can create a combined odor vector 321 based on the odorants 312. For instance, the smart nose 316 can create a first odor vector associated with a plurality of odors 312 received. An image recognition device 328 can scan an area including objects 1, 2, and 3 311 and collect video 314 and/or images of the objects 1, 2, and 3 311. The image recognition device 328 (e.g., a three-dimensional object detection device) can receive the video 314 or images and can run image recognition machine learning models based on the video 314 and/or images to identify and determine a list of predicted objects 326 present (e.g., list including objects 1, 2, and 3 311). The list of predicted objects 326 can include a plurality of identified objects based on the plurality of images collected by the image detection device 328.

The combined odor vector 321 and the list of predicted objects 326 can be fed into a refine odor vector device 322 which can utilize a machine learning model to map odorants 312 to objects 1, 2, 3 311 using an odor pattern database. The odor pattern database, in some examples, may be cloud-based or may be local to the device 350 and updated responsive to connection to the cloud-based odor pattern database (e.g., cloud storage 302).

In some examples, the refine odor vector device 322 may comprise a non-transitory machine-readable medium having instructions executable to refine an odor vector based on the identified plurality of objects and an odor pattern database (e.g., cloud storage 302, other database, and/or odor safety database 338) using a machine learning model. The refine odor vector device 322 can be in communication with an odor safety database 338, as illustrated at connection 1 325. The odor safety database 338 can include a list of substances with their corresponding odor vectors, for instance, unpleasant and/or dangerous substances with their corresponding odor vectors. When only a partial odor vector is present, the refine odor vector device 322 can correlate odor vectors to objects identified by the image recognition device 328 (e.g., objects 1, 2, and 3 311) to generate the refined odor vector 352, which includes a full odor vector.

The refined odor vector 352 can be fed into a machine learning decoder 318 for generation of a final object identification list 334, which is queried against the odor safety database 338 to identify a category of the odor (e.g., safe, unsafe, etc.). The machine learning decoder 318, in some examples, can include a non-transitory machine-readable medium having instructions executable to determine with which of the plurality of identified objects a particular odor of the plurality of odors (e.g., odorants 312) is associated by decoding the refined odor vector 352 using a machine learning model. The machine learning model can be updated in response to receipt of updates to the machine learning model, the odor pattern database, or both.

In some examples, the application and/or program 336 can include a non-transitory machine-readable medium having instructions executable to receive updates to the first machine learning model, the updates to the second machine learning model, and updates to the odor pattern database, for instance at 303 and 306 from the cloud storage 302 and the application 304. The application and/or program 336 can pass along the updates at 332-1, 332-2, for example. The particular odor of the plurality of odors can be compared to an odor block list (e.g., within odor safety database 338), and a determination of the association can be provided to a first device (e.g., a mobile device housing application 304), cloud storage 302, or both responsive to the particular odor not being on the odor block list. A block odor notification and the determination of the association can be provided to the first device (e.g., via an application 304), the cloud storage 302, or both responsive to the particular odor being on the odor block list.

The application and/or program 336 can activate an auto alert system 309 by sending a dangerous odor alert signal 346 in response to detection of a dangerous object and/or dangerous odor. In some instances, the device 350 may include a plurality of sensors to detect a plurality of unsafe odors (e.g., carbon monoxide, chemicals, etc.). Upon detection of one of the unsafe odors, an alert can be provided, for instance via the application 304 or the auto alert system 309. A user can validate the odor as unpleasant and/or dangerous in the application and/or program 336 (e.g., via the application 304), which can update the odor safety database 338 accordingly.

The application and/or program 336 can receive updates and feedback regarding the odorants 312. For instance, the cloud storage 302 can be updated with new and/or more accurate odor vectors, which can affect predictions 308 made regarding the odors 312. The updates, both to databases and machine learning models can be sent, at 30,3 to an application 304 utilized by the user, and then passed along, at 306, to the device 350. For instance, the application and/or program 336 can receive updates to machine learning models and send them to appropriate locations, for instance at 332-2 to update a machine learning model used at the machine learning decoder 318 and at 332-1 to update a machine learning model used in image recognition. The odor pattern database and/or the odor safety database 338 may be updated, for instance, responsive to a predicted odor being absent from the odor pattern database and/or the odor safety database 338, for instance via connection 1 325.

Other feedback can be sent to the device 350 at 307. For instance, if a user sees a prediction and believes it to be incorrect, the user can flag it in the application 304, and the feedback at 407 can be used to update the machine learning models at 332-1, 332-2. The application 304 can also take the predictions 308 and update the machine learning models, odor vectors, etc. stored in cloud storage 302 with the predictions at 301. For instance, the cloud storage 302 can be updated based on real time user experience and an electrical signature (e.g., a unique electrical signature) can be created for each image and smell detected and/or predicted. The odor safety database 338 may be updated, for instance, responsive to the predicted odor being absent from the odor safety database 338, for instance via connection 1 325 responsive to a request for the odor to be added to the odor safety database 338.

Figure 4:
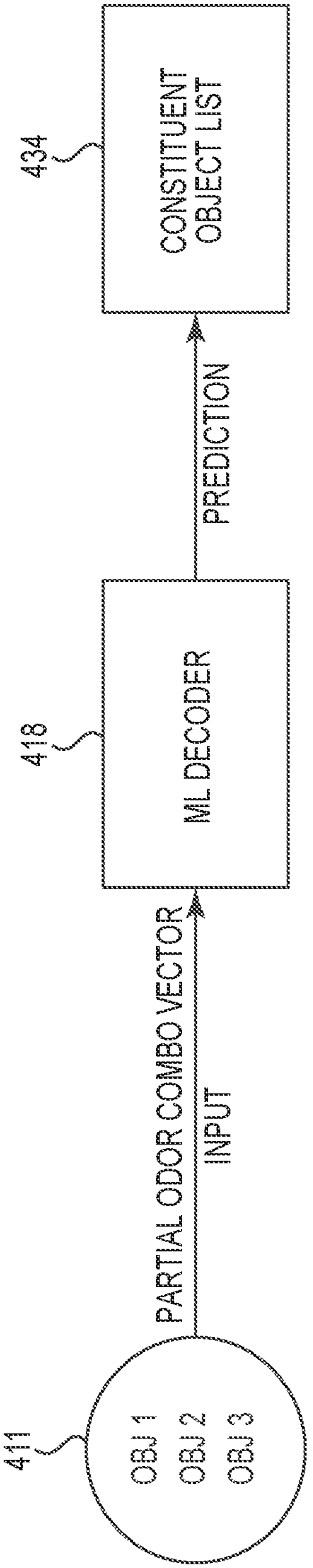
FIG. 4 is a flow diagram representing an example method for predicting an odor using a smart nose with machine learning in accordance with a number of embodiments of the present disclosure.

FIG. 4 is a flow diagram representing an example method for predicting an odor using a smart nose with machine learning in accordance with a number of embodiments of the present disclosure. FIG. 4 is an example of multiple odors in a single location having different odor vectors. In contrast, when a single object is present in an odor vector, it is a single odor vector. For instance, at 411, three objects having three different odors associated therewith create an odor vector. For example, object 1 may be cake, object 2 may be coffee, and object 3 may be a rose. Because multiple objects are present, the odor vector is a combination odor vector. In the example, illustrated in FIG. 4, only a partial signature for at least one of the objects is present, so the odor vector is a partial odor combination vector. A full odor combination vector may include all odorant molecules for the objects present in the odor vector.

The machine learning decoder 418 can take the partial odor combination vector, as well as image recognition data (e.g., images of object 1, object 2, and object 3), and predict a constituent object list 434. For instance, the partial odor combination vector can be intercepted from the smart nose device (e.g., smart nose device 216, 316) and refined with machine learning. For example, the machine learning model may recognize that a rose is present based on the partial odor combination vector and the image recognition data. Put another way, the machine learning model may determine based on the partial odor combination vector that object 3 is a flower, but the combination with the image recognition data allows for the more specific determination of a rose.

In some examples, when multiple odors are present, a machine learning model can be used to decode multiple odor vectors. For instance, full, partial, and combination odor vectors can be fed into the machine learning decoder 418, and the machine learning model is trained to break the different odor vectors into segments. Put another way, the model can be trained to recognize and distinguish into three different and recognizable odors for which activations pattern are known. These different odors can be recognized by the brain implant, for instance.

The machine learning decoder 418 can create the constituent object list of odors that are present (e.g., a comprehensive odor vector) which can be passed on to a cloud-based database for use in updating associated machine learning models and odor pattern databases. In the previous example, for instance, the constituent object list 434 may include cake, coffee, and rose. The constituent object list 434 can be compared to an odor block list, in some examples, if particular odors are to be blocked. This list, after comparison to the odor block list (and excluding blocked odors), can be passed on to a brain implant or an alert system as an activation pattern. A user can also provide feedback, for instance, if the prediction is incorrect. This feedback can be used to update machine learning models and odor block lists.

FIG. 5 is diagram including example machine learning model training inputs in accordance with a number of embodiments of the present disclosure. FIG. 5 illustrates input features 560 including odor vectors including 400 dimensions and associated odorants. "FV" indicates a full odor vector, "PV1" and "PV2" indicate different partial odor vectors, and "FV+FV", "FV+PV", and "PV+PV" indicate combination odor vectors. FIG. 5 also includes a prediction 562 made in response to a machine learning model receiving different input features 560. In some examples, the prediction can include a brain stimulation pattern generated by a smart nose for the predicted object or objects and associated odorants. A "1" in an odorant column indicates a presence of a specific odorant molecule, while a "0" indicates the absence of a specific odorant molecule.

For example, considering 5 of 400 dimensions for ease of explanation, if a full odor vector for a rose is [1,0,0,1,1], then possible partial odor vectors for rose can include [0,0,0,1,1], [1,0,0,1,0], or [1,0,0,0,0]. In such an example, some known odor molecules are absent. If a full odor vector for coffee is [0,1,1,1,0], a combination odor vector for rose and coffee is [1,0,0,1,1]+[0,1,1,1,0]=[1,1,1,1,1]. This combination odor vector is a vector of all odor molecules of both rose and coffee. In an example where at least one of the rose and the coffee odor vectors is partial, a resulting combination odor vector of the two is also partial.

Full odor vectors, partial odor vectors, full combination odor vectors, and partial combination odor vectors are used as input into a machine learning model, for example as illustrated at 418 of FIG. 4, with a prediction 562 of objects present made by the machine learning model. In the example illustrated in FIG. 5, full odor vectors, partial odor vectors, full combination odor vectors, and partial combination odor vectors associated with cake and a rose are input features 560 used to train and update a machine learning model for predicting odors detected using a smart nose along with an image recognition device.

The input features 560 include refined odor vectors of the full odor vectors, partial odor vectors, full combination odor vectors, and partial combination odor vectors. These refined odor vectors can be provided to the machine learning decoder, which determines a list of odors (e.g., prediction 562) as a comprehensive odor vector. This can be provided to the application and/or program (e.g., application and/or program 236, 336) that can be in communication with a machine learning model in external storage (e.g., cloud storage 202, 302) via an application (e.g., application 204, 304). In such an example, if a new (e.g., unrecognized) odor is detected that is not present in local storage, the application can communicate, when a communication path is available, with the machine learning model in the outside storage to update the local storage and machine learning models associated with the smart nose and image recognition devices. Final odor predictions that consider odor vectors and image recognition determinations can be sent to a brain implant or used to create alerts (e.g., dangerous odor alerts).

Figure 6:
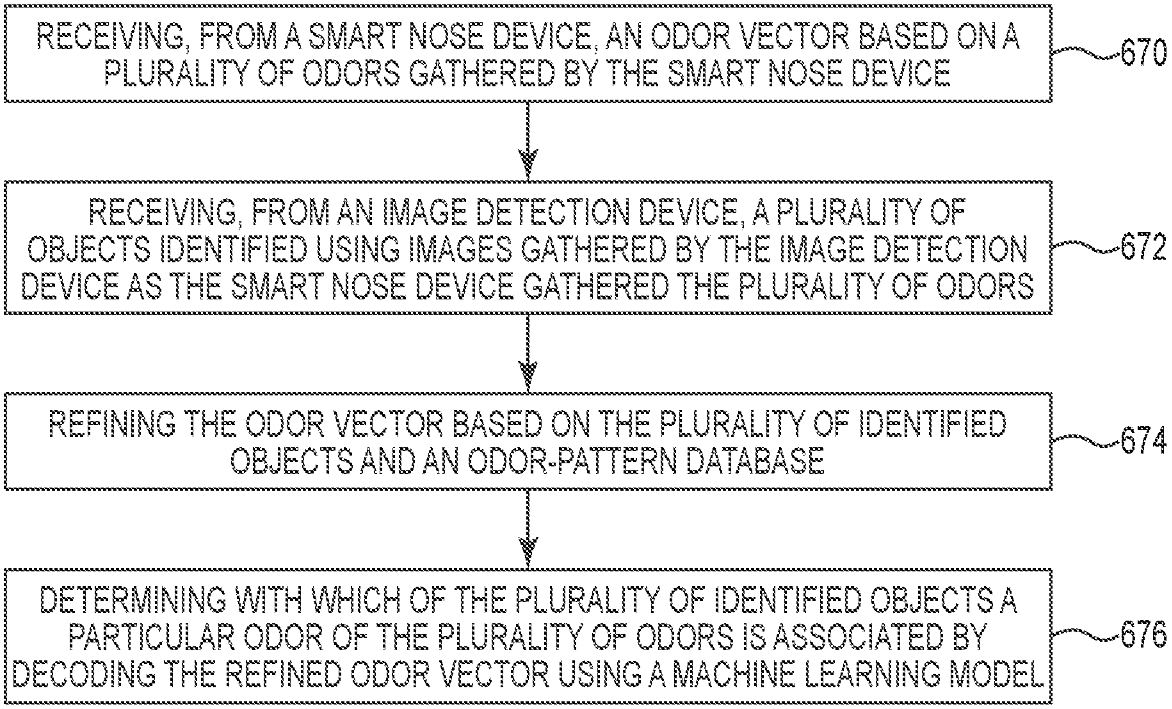
FIG. 6 is another flow diagram representing an example method for a smart nose with machine learning in accordance with a number of embodiments of the present disclosure.

FIG. 6 is another flow diagram representing an example method for a smart nose with machine learning in accordance with a number of embodiments of the present disclosure. The example method may be performed, in some examples, using a system and/or apparatus such as those described with respect to FIGS. 1, 2, and 3.

At 670, the method can include receiving, from a smart nose device, an odor vector based on a plurality of odors gathered by the smart nose device. For instance, the smart nose device may receive a combination odor vector that includes full and/or partial odor vectors associated with cake, roses, and coffee.

At 672, the method can include receiving, from an image detection device, a plurality of object determinations identified using images gathered by the image detection device as the smart nose device gathered the plurality of odors. For example, as the smart nose device gathers the combination odor vector, the image detection device can gather images and determine what those images are. For instance, the image detection device may determine that as the odor vectors are gathered by the smart nose device, objects present include cake, roses, and a table.

The method, at 674 can include refining the odor vector based on the plurality of object determinations and an odor-pattern database. For instance, the smart nose can utilize a local and/or external odor pattern database to determine likely sources associated with the odor vector by comparing the odor vector to odor vectors in the odor-pattern database. A machine learning model can compare the determinations of the likely sources to the images detected by the image detection device. In the example, no coffee was detected by image detection device and no table odor was identified by the smart nose. As such, the machine learning model may determine a refined odor vector includes a combination vector of roses and cake.

Put another way, refining the odor vector can include creating a combined odor vector including the plurality of odors, creating an object list including the plurality of object determinations, mapping the object list to the combined odor vector, and generating the refined odor vector. The refined odor vector can be used as input into a machine learning model to decode the refined odor vector to determine a final object list.

At 676, the method can include determining with which of the plurality of object determinations a particular odor of the plurality of odors is associated by decoding the refined odor vector using a machine learning model. For example, decoding the refined odor vector can include generating a final identification object list. In keeping with the previous example, odor vectors associated with the cake can be identified and odor vectors associated with the roses can be identified using the machine learning model, which considers the refined odor vector and the images detected. In some examples, decoding the refined odor vector can include comparing the final identification object list to an odor block list. In other examples, the comparison to the odor block list is not part of the decoding.

The odor block list can include, for instance, dangerous odors and/or odors a user has chosen not to detect. For instance, a user may get nauseous each time a particular odor is detected and may desire to block this odor. In another example, a manufacturing plant may provide an alert to workers if a dangerous odor is detected based on the comparison. Approved (e.g., not on the odor block list) odors can be allowed.

Determination of the particular odor can be provided to a brain implant coupled to the smart nose device responsive to the particular odor being absent from an odor block list and blocking the determination of the particular odor from being provided to the brain implant coupled to the smart nose device responsive to the particular odor being on the odor block list. In some instances, an alert can be provided responsive to the particular odor being on an odor block list.

For example, an activation pattern associated with an object on the final identification object list that is not on the odor block list can be retrieved, and the activation pattern can be sent to a brain implant associated with the smart nose, in some examples. Similar, an activation pattern associated with an object on the final identification object list that is on the odor block list can be retrieved, and the activation pattern can be blocked from being sent to the brain implant associated with the smart nose, in some examples. In an example where no brain implant is present, an alert may be provided (e.g., alarm, message, etc.) when an object on the final identification object list that is on the odor block list.

The machine learning model, in some examples, can be updated in response to receipt of an additional odor, an additional image (e.g., object determination), or both. For instance, if a new odor is detected by the smart nose and/or a new object is detected by the image detection device, the machine learning model can be updated accordingly based on the odor pattern database. For instance, if the smart nose detects cinnamon, and the image detection device recognizes a roll, a new refined vector can be created, and the machine learning model can be trained and updated with the new information to detect a cinnamon roll. Similarly, odor vectors can be updated responsive to receipt of an additional odor, an additional image, or both.

In other examples, the machine learning model can be updated based on user feedback received via a computer application and responsive to the determination of the particular odor. For example, if the user knows he or she is consuming a caramel roll, but the machine learning model identified the object as a cinnamon biscuit, a user can provide feedback (e.g., via a device application), to train the machine learning model that the odor and/or images associated with that object should be identified as a caramel roll.

In yet other examples, the machine learning model can be updated responsive to receipt from a different database of an update to the machine learning model, the odor pattern database, or both. For example, the different database may be a cloud-based database that updates a device application and associated data when they are in communication with one another. For instance, a user may not have internet access at a particular location, but once the user has internet access, the different database can update a local odor pattern database and the associated machine learning model.

Although specific embodiments have been illustrated and described herein, those of ordinary skill in the art will appreciate that an arrangement calculated to achieve the same results can be substituted for the specific embodiments shown. This disclosure is intended to cover adaptations or variations of one or more embodiments of the present disclosure. It is to be understood that the above description has been made in an illustrative fashion, and not a restrictive one. Combination of the above embodiments, and other embodiments not specifically described herein will be apparent to those of skill in the art upon reviewing the above description. The scope of the one or more embodiments of the present disclosure includes other applications in which the above structures and processes are used. Therefore, the scope of one or more embodiments of the present disclosure should be determined with reference to the appended claims, along with the full range of equivalents to which such claims are entitled.

In the foregoing Detailed Description, some features are grouped together in a single embodiment for the purpose of streamlining the disclosure. This method of disclosure is not to be interpreted as reflecting an intention that the disclosed embodiments of the present disclosure have to use more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A system, comprising:
- a smart nose device configured to:
  - receive an odor via a plurality of sensors for different odor receptors; and
  - create a first odor vector associated with the odor;
- an image detection device configured to:
  - receive a plurality of images while the odor is received; and
  - identify a plurality of objects within the plurality of images in a presence of the received odor; and
- a computing device to:
  - refine the first odor vector based on the identified plurality of objects;
  - create, utilizing a machine learning model, a second odor vector based on the refined first odor vector and an odor pattern database;
  - predict the odor based on the second odor vector; and
  - update the machine learning model responsive to receipt, from a different, cloud-based odor pattern database, of an update to the machine learning model, an update to the odor pattern database, or both.

2. The system of claim 1, comprising the computing device to further refine the first odor vector, update the machine learning model, and update the second odor vector in response to receipt of an additional odor, an additional image, or both.

3. The system of claim 1, wherein the odor pattern database is a cloud-based odor pattern database.

4. The system of claim 1, wherein the odor pattern database is local to the system and is updated responsive to connection to a different, cloud-based odor pattern database.

5. The system of claim 1, comprising the computing device to block the predicted odor based on a comparison of the second odor vector to an odor block list.

6. The system of claim 1, comprising the computing device to update the odor pattern database responsive to the predicted odor being absent from the odor pattern database.

7. A method, comprising:
receiving, from a smart nose device, an odor vector based on a plurality of odors gathered by the smart nose device via a plurality of sensors for different odor receptors;
receiving, from an image detection device, a plurality of object determinations identified using images gathered by the image detection device in a presence of the gathered plurality of odors as the smart nose device gathered the plurality of odors;
refining the odor vector based on the plurality of object determinations and an odor pattern database;
determining with which of the plurality of object determinations a particular odor of the plurality of odors is associated by decoding the refined odor vector using a machine learning model; and
updating the machine learning model in response to receipt of an additional odor, an additional object determination, or both.

8. The method of claim 7, comprising:
providing the determination of the particular odor to a brain implant coupled to the smart nose device responsive to the particular odor being absent from an odor block list; and
blocking the determination of the particular odor from being provided to the brain implant coupled to the smart nose device responsive to the particular odor being on the odor block list.

9. The method of claim 8, wherein:
refining the odor vector comprises:
creating a combined odor vector including the plurality of odors;
creating an object list including the plurality of object determinations;
mapping the object list to the combined odor vector;
generating the refined odor vector; and
decoding the refined odor vector comprises:
generating a final identification object list; and
comparing the final identification object list to an odor block list.

10. The method of claim 9, comprising:
retrieving an activation pattern associated with an object on the final identification object list that is not on the odor block list; and
sending the activation pattern to a brain implant associated with the smart nose.

11. The method of claim 9, comprising:
retrieving an activation pattern associated with an object on the final identification object list that is on the odor block list; and
blocking the activation pattern from being sent to a brain implant associated with the smart nose.

12. The method of claim 7, further comprising providing an alert responsive to the particular odor being on an odor block list.

13. The method of claim 7, comprising updating the machine learning model in response to receipt from a different database of an update to the machine learning model, the odor pattern database, or both.

14. The method of claim 7, comprising updating the machine learning model based on user feedback received via a computer application and responsive to the determination of the particular odor.

15. An apparatus, comprising:
a smart nose device configured to create a first odor vector associated with a plurality of odors collected via a plurality of sensors for different odor receptors;
an image detection device configured to identify a plurality of objects based on a plurality of images collected by the image detection device and in a presence of the received plurality of odors;
a first non-transitory machine-readable medium having first instructions executable to:
refine the first odor vector based on the identified plurality of objects and an odor pattern database using a first machine learning model; and
a second non-transitory machine-readable medium having second instructions executable to:
determine with which of the plurality of identified objects a particular odor of the plurality of odors is associated by decoding the refined first odor vector using a second machine learning model; and
update the second machine learning model in response to receipt, from a different, cloud-based odor pattern database, of updates to the second machine learning model, the odor pattern database, or both; and
a third non-transitory machine-readable medium having third instructions executable to:
receive updates to the first machine learning model, the updates to the second machine learning model, and the updates to the odor pattern database;
compare the particular odor of the plurality of odors to an odor block list;
provide the determination of the association to a first device, cloud storage, or both responsive to the particular odor not being on the odor block list; and
provide a block odor notification and the determination of the association to the first device, the cloud storage, or both responsive to the particular odor being on the odor block list.

16. The apparatus of claim 15, wherein the first odor vector is a partial odor vector.

17. The apparatus of claim 15, wherein the odor pattern database is a cloud-based odor pattern database, and the apparatus comprises a different odor pattern database local to the system that is updated responsive to connection to the cloud-based odor pattern database.

18. The apparatus of claim 15, comprising:
a different plurality of sensors to detect a plurality of unsafe odors; and
the third instructions to provide an alert via the apparatus in response to detection of one of the plurality of unsafe odors.

* * * * *